(12) United States Patent
Honkura et al.

(10) Patent No.: US 7,748,982 B2
(45) Date of Patent: Jul. 6, 2010

(54) DENTURE ATTACHMENT

(75) Inventors: Yoshinobu Honkura, Aichi (JP); Kazuo Arai, Aichi (JP); Eiki Kikuchi, Aichi (JP); Yuh-yuan Shiau, Taipei (TW); Che-tong Lin, Taipei (TW)

(73) Assignee: Aichi Steel Corporation, Tokai-shi (JP)

( * ) Notice: Subject to any disclaimer, the term of this patent is extended or adjusted under 35 U.S.C. 154(b) by 690 days.

(21) Appl. No.: 10/545,954

(22) PCT Filed: Feb. 16, 2004

(86) PCT No.: PCT/JP2004/001662

§ 371 (c)(1),
(2), (4) Date: Aug. 17, 2005

(87) PCT Pub. No.: WO2004/082513

PCT Pub. Date: Sep. 30, 2004

(65) Prior Publication Data

US 2007/0037124 A1   Feb. 15, 2007

(30) Foreign Application Priority Data

Feb. 17, 2003   (JP) ............................. 2003-038582

(51) Int. Cl.
*A61C 13/235* (2006.01)
(52) U.S. Cl. ..................................................... 433/189
(58) Field of Classification Search ................. 433/189, 433/182, 181; 24/304
See application file for complete search history.

(56) References Cited

U.S. PATENT DOCUMENTS

| 4,202,097 | A | * | 5/1980 | Erlich-Deguemp | .......... 433/189 |
| 5,123,843 | A | * | 6/1992 | Van der Zel et al. | ......... 433/189 |
| 5,788,493 | A | * | 8/1998 | Tanaka et al. | ................ 433/189 |
| 6,299,450 | B1 | * | 10/2001 | Honkura et al. | ............. 433/189 |
| 2002/0115041 | A1 | * | 8/2002 | Kyotani et al. | .............. 433/189 |

FOREIGN PATENT DOCUMENTS

| JP | 05-068688 | 3/1993 |
| JP | 06-86715 | 12/1994 |
| JP | 07-136190 | 5/1995 |
| JP | 08-150156 | 6/1996 |
| JP | 10-127663 | 5/1998 |
| JP | 2002-102258 | 4/2002 |
| JP | 2002-186630 | 7/2002 |
| JP | 2002-325778 | 11/2002 |
| WO | WO 01/66034 A1 * | 9/2001 |

* cited by examiner

*Primary Examiner*—Cris L Rodriguez
*Assistant Examiner*—Sunil K Singh
(74) *Attorney, Agent, or Firm*—Oblon, Spivak, McClelland, Maier & Neustadt, L.L.P.

(57) ABSTRACT

A dental attachment includes a magnet element delivering a magnetic attraction force, a yoke made of a soft magnetic material and having a recess for housing the magnet element, and a disc consisting of the soft magnetic material and joined to the yoke so as to close the opening of the recess with the magnet element housed in the recess. The yoke has an almost disc shape and has collars protruding radially outwardly from the outer peripheral surface thereof. The collars are formed to be separated in at least two locations in a substantially peripheral direction, and non-protruding portions having radially outward projection amounts of zero or up to 50% of the maximum projection amount at the collars are provided between respective collars.

12 Claims, 10 Drawing Sheets

DENTURE ATTACHMENT

TECHNICAL FIELDS

The present invention relates to a dental attachment which is used so as to embed a denture by magnetic attractive force.

BACKGROUND ART

In dental treatment, as is shown in patent document 1, because of the easiness of putting on or removing, various dental attachments which utilize magnetic attractive force have been proposed.

A dental attachment 91 housed a magnetic body is, as is shown in FIG. 19, embedded in dental base 810 fixed a denture 81. On the tooth root side, a keeper 92 made of a soft magnetic material is embedded in a root cap 82 or an implant (FIG is abbreviated). By this, the denture housed the dental attachment 91 can be fixed to the keeper 92 by the magnetic attractive force.

The dental attachment 91 is fixed to the dental base 810 with adhesive of room temperature polymerization resin etc. The fitting strength greatly influences the endurance of the whole denture 81 which houses the dental attachment 91. Therefore, to improve the fitting strength between the dental attachment and the dental base, making a part protruding radially outward from the outer peripheral surface thereof, a so-called under cut effect thereof is proposed (See patent document 2).

[patent document 1]: Japanese Unexamined Patent Application Publication No. 7-136190

[patent document 2]: Japanese Unexamined Utility Model Application Publication No. 6-86715

When the dental attachment is fixed in the dental base, it is necessary to prepare an adhesive in a hole of the dental base beforehand, push the dental attachment by giving a stress on it and make the adhesive go around as far as the outer peripheral surface. In contrast, when only a protruding part is made, as in the prior art, the protruding part prevents the fluidity of adhesive and without exerting enough under cut effect, the connecting strength can not be improved much.

Still, in this structure, when the turning force to turn relatively is added between the dental base and the dental attachment, the problem that the dental attachment turns more easily relative to the dental base is generated because the outer peripheral surface of the dental attachment and the protruding part are constructed in a concentric configuration.

To solve prior problems, the present invention provides a dental attachment that is greatly improved over prior objects in fixing strength and can more effectively prevent turning to the dental base.

SUMMARY OF THE INVENTION

The present invention of the dental attachment configured to be embedded in a denture base so as to face a keeper made of soft magnetic material in a tooth root, the dental attachment comprises:

a magnetic element delivering magnetic attractive force, a yoke made of a soft magnet material and having the recess for housing the magnetic element, and a disk joined so as to close the opening of a recess with the magnet element housed in the recess, wherein the yoke has an almost circular disk shape and collars protruding radially outward from a outer peripheral surface thereof, the collars are formed to be separated in at least two locations in a substantially peripheral direction, and non-protruding parts having radially outward projection amounts of zero or up to 50% of the maximum projection amount at the collars are provided between respective collars.

The present invention has not only the collars protruding from the outer peripheral surface of the yoke but also the non-protruding portions. The collars are formed to be separated in at least two locations in a substantially peripheral direction, and non-protruding portions are provided between respective collars. 'Substantially' means that the case in which the non-protruding portions are a little projected and connected with collars is included in the notion that respective collars are formed to be separated.

In the present invention, because of the existence of both the collars and the non-protruding portion, the following excellent operation effect is exerted.

That is, in the case of connecting the dental attachment to the dental base, adhesive is applied in the hole provided on the dental base beforehand, the surface of the dental attachment (surface of opposite side to the surface which provides the recess) is contacted and pushed to this adhesive, and adhesive is fluidized. At this time, because there are the collars and the non-protruding portions on the outer peripheral surface of the dental attachment, the adhesive tries to flow to the outer peripheral surface of the yoke with passing collars and non-protruding portions.

However, because the collars protrude radially outward, as long as adhesive which came over the collars flows radially inward, adhesive does not reach the outer peripheral surface of the yoke. On the other hand, because of the non-protruding portion having projection amounts of zero or very little, the adhesive passes the non-protruding portion and contacts the outer peripheral surface of the yoke almost without resistance and also flows easily to the peripheral direction. By flowing to the peripheral direction, the adhesive sufficiently contacts the outer peripheral surface facing the collars. That is, by the existence of the non-protruding portions, the adhesive flows sufficiently to the back of the collars and the collars are embedded sufficiently in the adhesive. Therefore, undercut effect at the collars is sufficiently exerted.

Therefore, the dental attachment of the present invention can greatly improve the connecting strength over the prior dental attachments.

Furthermore, due to plural protruding portions of the collars, even when the force to turn relatively is added between the dental base and the dental attachment, the relative turn can be prevented by fitting the collars and the adhesive.

The non-protruding portions have, as mentioned above, radially outward projection amounts of zero or up to 50% of the maximum projection amount at the collars. If the projection amount is over 50% of the maximum projection amount at the collars, the mentioned fluidity of the adhesive by the existence of non-protruding portions cannot be adequately secured.

BEST MODE FOR CARRYING OUT THE INVENTION

Figure 1:
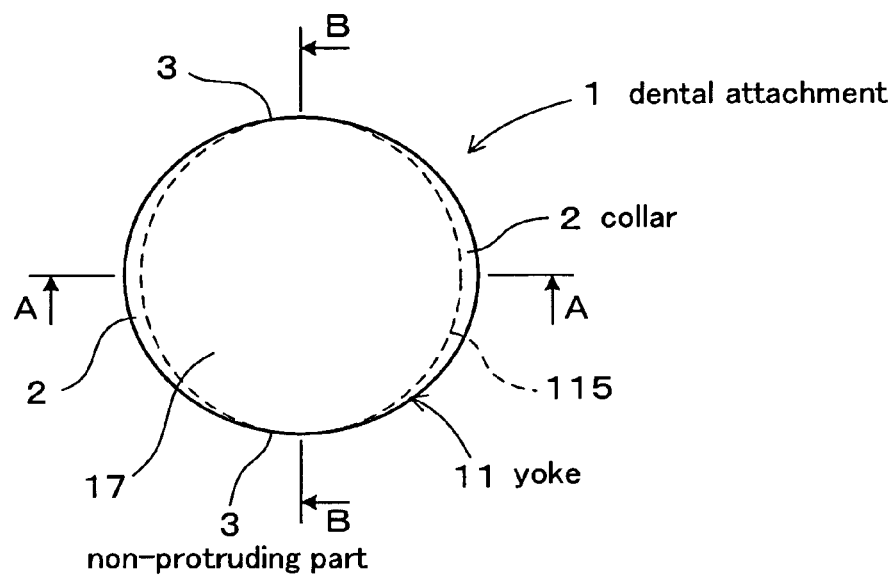
FIG. 1 is a plane view of the dental attachment of embodiment 1.

As the soft magnetic material constituting the yoke in the present invention, various magnetic materials are available, for example, 17Cr-based stainless steel, 17Cr-2Mo-based stainless steel, and 19Cr-2Mo-based stainless steel etc. are preferable. These are excellent in resisting corrosion and the durability of the dental attachment can be improved.

As the magnetic element housed in the yoke, a magnet with high magneto motive force per unit volume is used. Specifically, for example Sm—Co-based or Nd—Fe—B-based rare earth magnets with high energy product are preferable.

The disk can be made of the non-magnetic material, but a soft magnetic material is preferable, considering magnetic properties. As an available soft magnetic material for the disk in this case, various soft magnetic material is possible, and the same material as the yoke is also possible.

Also, it is preferable for the disk to be connected with the yoke through a non-magnetic portion.

The yoke made of the soft magnetic material and the disk made of the soft magnetic material can connect directly but, as is shown in embodiments, the intervention of the non-magnetic material can prevent direct magnetic flux from the disk to the yoke and magnetic absorbing force can be improved.

Connecting the disk to the yoke can be done by for example welding and the welding portion can be made of the non-magnetic material.

For example, as materials for the ring portion between the yoke and the disk, non-magnetic stainless steel (for example, SUS316L) etc., which are the non-magnetic anticorrosive material, can be used and well-known art that the yoke, a ring material and the disk are welded at one or two welding points by laser welding is available.

To get stable non-magnetism of a welding portion, separately, it is enough to add the element to stabilize the austenite system. For one example, well-known art, the adding of only Ni or Ni—Cr alloy is available. As a way to add, those materials can be intervened between non-magnetic stainless steel and the yoke or the disk, or they can be added directly by wire etc. during melting, but the method of adding materials is limited to these methods.

Moreover, there is a way to make non-magnetism by direct addition of Ni or Ni—Cr alloy etc. to make non-magnetism between the yoke and the disk. But with this method, there is not enough stability of non-magnetism.

Also, the outer peripheral shape of the yoke is almost a round shape and the outer peripheral shape surrounding the collar and the non-protruding port is almost an oval shape and it is preferable that a pair of the collars is formed in the major axis direction of the oval shape and a pair of the non-protruding portion is formed in the minor axis.

In this case, because of the existence of two non-protruding portions formed in the minor axis, the fluidity effect of adhesive can be adequately secured, and by two collars formed in the major axis, enough under cut effect can be secured. Especially, in the case that a hole formed in the dental base is round in shape, because the distance of the non-protruding portion and the wall of the hole is larger than the distance between the collars in the major axis and the wall of the hole, the fluidity of the adhesive through the non-protruding portion can be improved.

Also the outer shape of the yoke is almost round, and the outer shape surrounding the collars and the non-protruding portion has a bigger diameter than the yoke, and the outer peripheral shape of almost round shape of concentric circles which is cut by plural tangents contacting the outer peripheral surface of the yoke. It is preferable that the part which is not cut and left is the collars and the part which is cut is the non-protruding portion.

Specifically, as follows, the shape shown in embodiment 2 and the other shapes are possible. In this case, the same operating effect as the above can be secured.

Embodiment 1

A dental attachment in the embodiment of the present invention is explained by using FIG. 1-FIG. 4.

Figure 2:
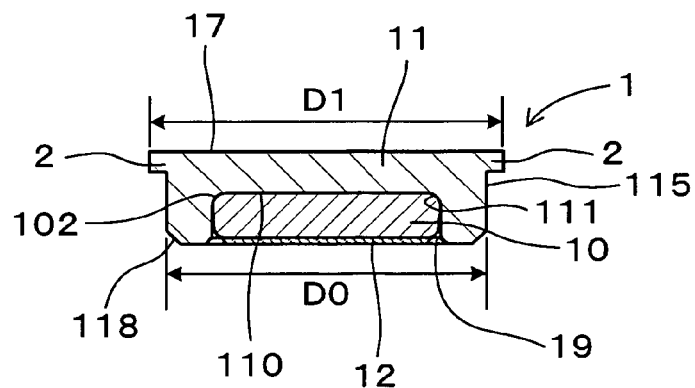
FIG. 2 is a cross section view of arrowed A-A of FIG. 1.
Figure 3:
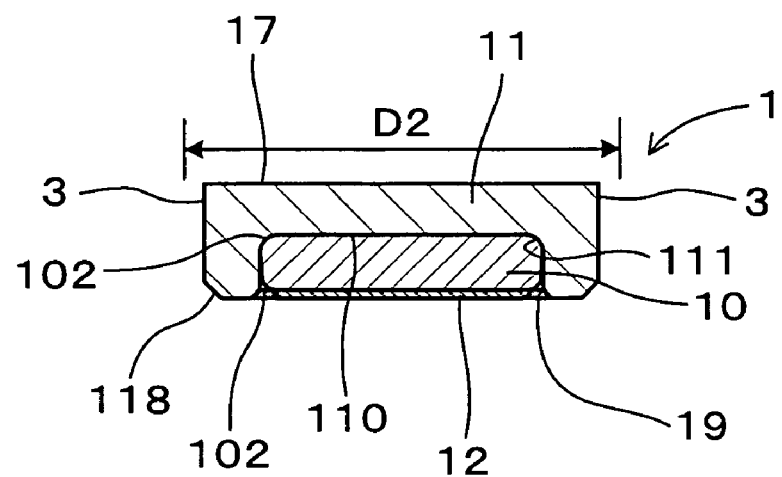
FIG. 3 is a cross section view of arrowed B-B of FIG. 1.
Figure 19:
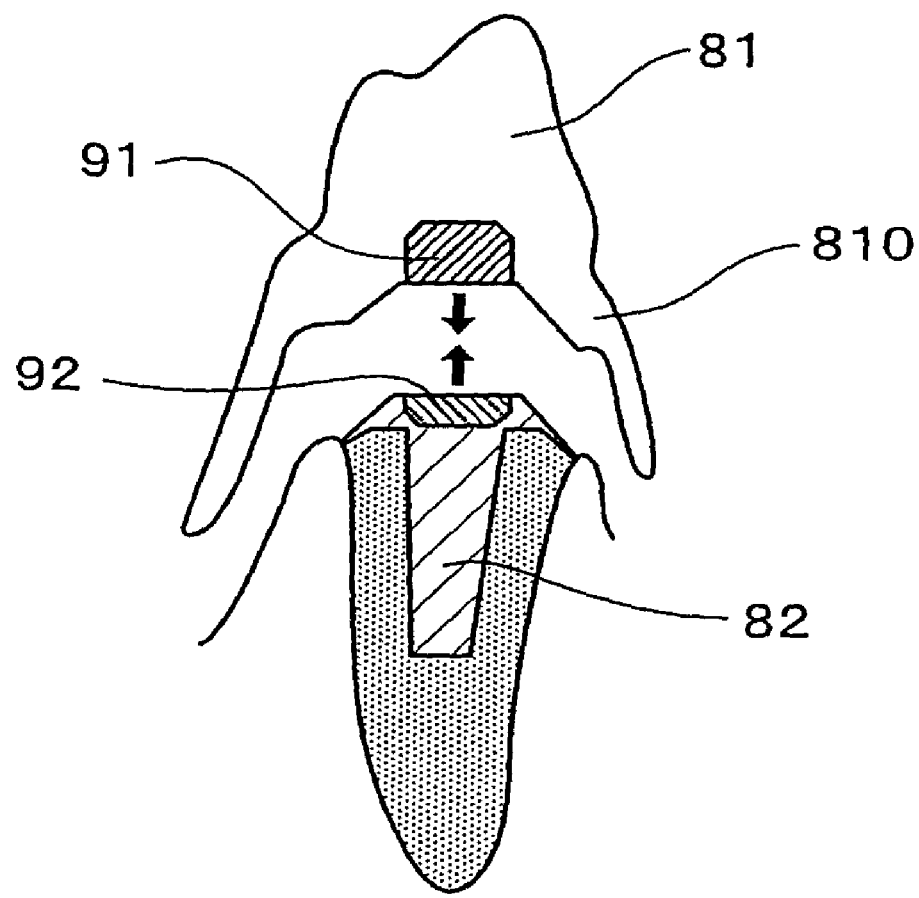
FIG. 19 is a diagram showing the example of using the dental attachment in a prior example.

A dental attachment 1 in this example, as is shown FIG. 1~FIG. 3, is embedded in a dental base 810 (FIG. 4) to face a keeper made of a soft magnetic material in a tooth root (FIG. 19).

The dental attachment 1 is, as is shown FIG. 2 and FIG. 3, composed of a magnetic element 10 delivering magnetic attractive force, a yoke 11 made of the soft magnetic material which has a recess 110 housing the magnetic element, a disk 12 which is made of the soft magnetic material and installed so as to close the opening of the recess 110 with the magnetic element 10 housed in the recess 110.

The yoke 11 is almost disk shaped and has collars 2 protruding radially outwardly from the outer peripheral surface 115.

Collars 2 are formed to be separated in at least two locations in a substantially peripheral direction, and between respective collars 2, the non-protruding portion 3 having radially outward projection amounts of zero are provided.

The following describes this in further detail.

As is shown in FIG. 1-FIG. 3, the outer peripheral shape of the yoke 11 is almost round in the dental attachment 1 of this example. As is shown in FIG. 1, the outer peripheral shape surrounding collars 2 and the non-protruding portion 3 is almost oval, and a pair of the collars 2 is formed in the major axis direction of the oval shape and a pair of the non-protruding portion 3 is formed in the minor axis direction.

The yoke 11, made of the soft magnetic material, 19Cr-2Mo-0.2 Ti—Fe, is made by machining. The specific size is as is shown in FIG. 1 and FIG. 2; the outer diameter D0 of the yoke is 4.4 mm, the major axis D1 of the oval including collars 2 and the non-protruding portion 3 is 4.9 mm, the minor axis D2 is the same 4.4 mm as the outer shape D0 of the yoke 11. That is, the maximum projection amounts of collars 2 is 0.25 mm and the projection amounts of the non-protruding portion 3 is zero.

The yoke 11 has the recess 110 made by machining to house magnetic element 10. The inner diameter of the recess 110 is 3.10 mm corresponding to the outer diameter of the magnetic element 10 mentioned below, an inner shoulder portion 111 has R part with the radius of curvature of 0.2 mm. Also, the edge of the outer periphery of the surface having recess 110 has a taper-shaped chamfer 118.

For the magnetic element 10, an Nd—Fe—B based permanent magnet which is (BH) max=42 MGOe is used. The magnet element 10 has a columnar shape with 3.05 mm outer diameter and 0.6 mm height, and the corner of its top and bottom peripheral surface 102 is formed to be R part which has 0.2 radius of a curvature.

For the disk 12, a disk made of the soft magnetic material, 19Cr-2Mo-0.2Ti—Fe, is used. After the magnetic element 10 is inserted in the recess 110 of the yoke 11, the disk is inserted and the edge of the outer periphery is welded to the yoke 11 and a welding portion 19 is made. The welding portion 19 is non-magnetic. More specifically, the ring material made of non-magnetic stainless steel (SUS316L), which is non-magnetic and anticorrosive material, is installed between the yoke 11 and the disk 12, and these are welded by laser welding.

Next, the method for connecting the dental attachment 1 having a structure like this to a dental base 810 is briefly explained.

Figure 4:
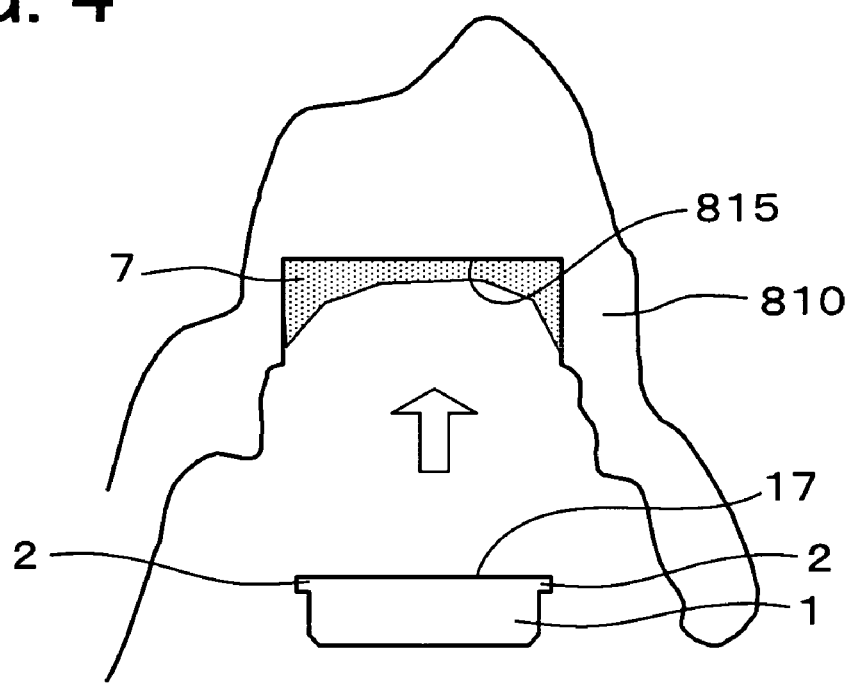
FIG. 4 is a diagram for explaining the method of fitting a dental attachment to a dental base.

As shown in FIG. 4, in advance, the hole 815 for disposing the dental attachment 1 is constructed on the dental base 810. Inner diameter of the hole 815 is about 0.6 mm bigger than, for example, the maximum outer shape of the dental attachment 1, that is, the major axis of oval with collars 2. The depth of the hole 815 is, for example, about 0.3 mm bigger than the thickness of the entire dental attachment 1.

The hole 815 is equipped with suitable amounts of the adhesive 7. As the adhesive 7, for example, polymetacrylate (PMMA), which is room temperature polymerization resin, is used. With the surface 17 of the dental attachment 1 (the surface opposite to the surface having the recess 110) faced to the hole 815 and advanced, the surface 17 of the dental attachment 1 is contacted to the adhesive 7. Still, by pushing forward the dental attachment 1, the adhesive 7 is flowed.

At this moment, the adhesive 7 in the hole 815 begins to flow from the surface side of the dental attachment 1 to outer peripheral surface of the yoke 11. Meanwhile, the dental attachment 1 of the present example, as is mentioned above, has a pair of collars 2 and a pair of non-protruding portions 3. Because collars 2, as is mentioned above, protrudes radially outwardly as long as the adhesive 7, which flows over this, does not flow radially inward, it does not reach the outer peripheral surface 115 of the yoke 11. Meanwhile, because the non-protruding portion 3 has zero projection amounts from the outer peripheral surface 115 of the yoke 11, the adhesive 7 passes through the non-protruding portion 3 and contacts the outer peripheral surface 115 of the yoke 11 almost without resistance and flows easily to the peripheral direction. Due to this flowing to the peripheral direction, the adhesive 7 sufficiently contacts the outer peripheral surface 115 facing collars 2.

Therefore, collars 2 are sufficiently embedded in the adhesive 7. So, the undercut effect in collars 2 can be exerted enough. Therefore, the dental attachment 1 can greatly improve the connecting strength with the dental base 810 over the prior dental attachments.

Also, collars 2 of the present embodiment are made in plural positions and the whole shape is oval shape. Therefore, even when the turning force is added between the dental base 810 and the dental attachment 1 to turn relatively thereof, the fitting between collars 2 and the adhesive 7 can prevent relative turning.

Still, though, in this example, the non-protruding portion 3 does not protrude in the radial direction at all; if the projection amounts are less than 50% of the maximum projection amounts of collars 2, protruding in the radial direction can get the same operating effect.

Embodiment 2

Figure 5:
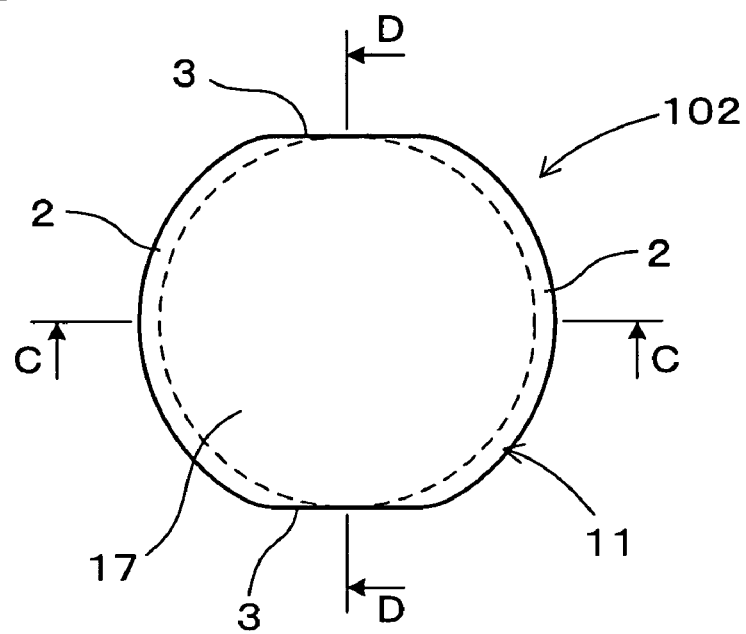
FIG. 5 is a plane view of the dental attachment of embodiment 2.
Figure 6:
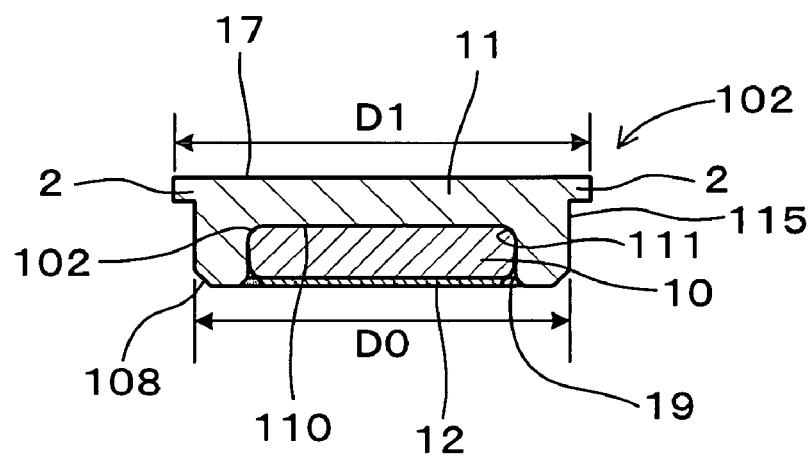
FIG. 6 is a cross section view of arrowed C-C of FIG. 5.
Figure 7:
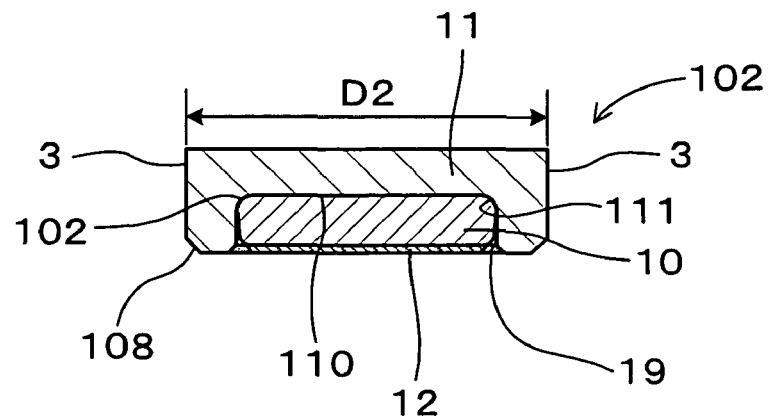
FIG. 7 is a cross section view of arrowed D-D of FIG. 5.

The present example, as is shown in FIG. 5~FIG. 7, changes the shape of collars portion 2 of the embodiment 1.

A dental attachment 102 of the present example has an almost round outer shape of the yoke 11. Also, the outer shape surrounding collars 2 and the non-protruding portion 3 has a bigger diameter than the yoke 11 and the outer peripheral shape of the almost round shape of the concentric circle has a shape which is cut by two plural tangents contacting the outer peripheral surface 115 of the yoke 11. Also, the opposite parts, which are not cut and left, are a pair of collars 2, and the parts which are cut are a pair of the non-protruding portion 3. The maximum outer diameter D1 including collars 2 and the outer diameter D2 of the non-protruding portion 3 in this example has the same as the size of D1 and D2 of the embodiment 1. The others are the same as the embodiment 1.

Because the dental attachment 1 of this example has the non-protruding portion 3, an operating effect similar to that of the embodiment 1 can be secured. Furthermore, because the outer shape of collars 2 has an arc shape of almost concentric circle of the yoke 11, the processing can be relatively easily done.

Embodiment 3

Figure 8:
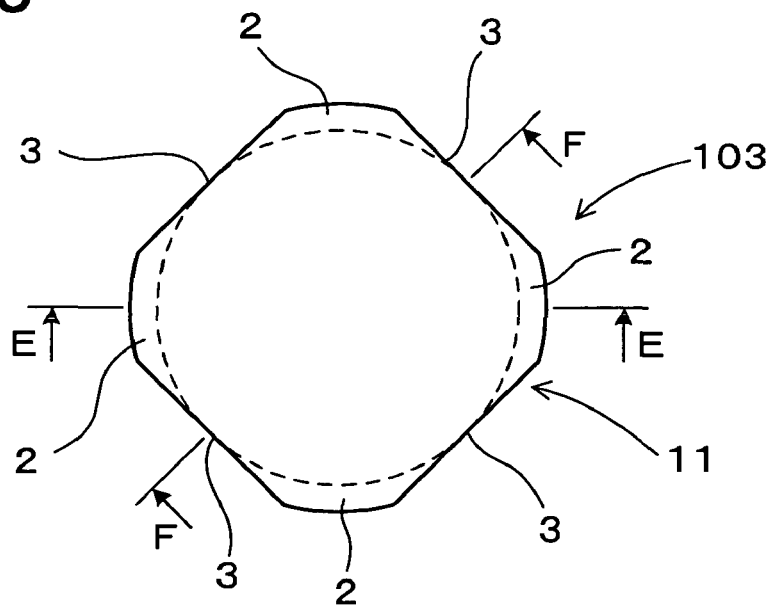
FIG. 8 is a plane view of the dental attachment of embodiment 3.
Figure 9:
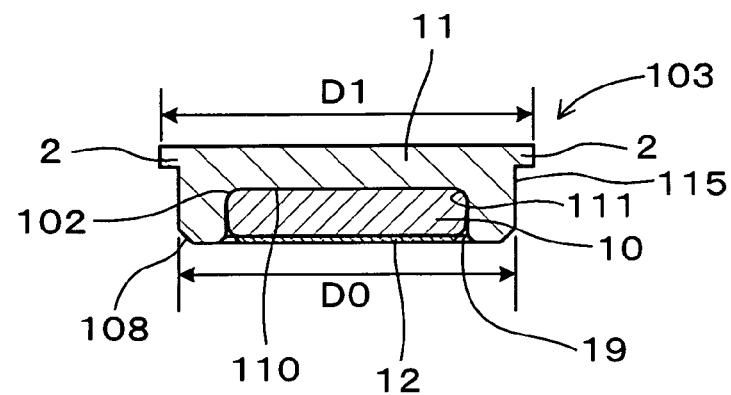
FIG. 9 is a cross section view of arrowed E-E of FIG. 9.
Figure 10:
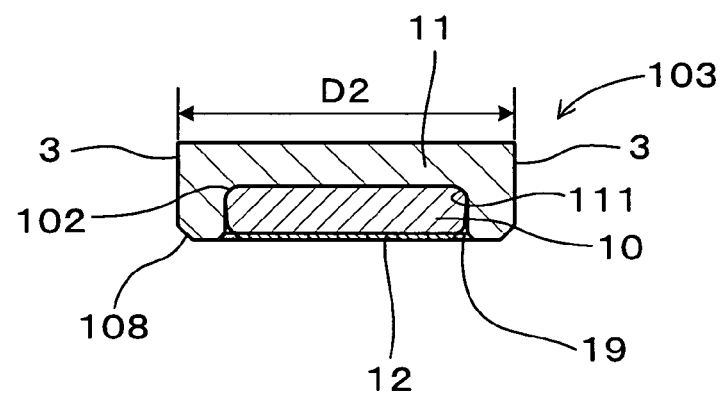
FIG. 10 is a cross section view of arrowed F-F of FIG. 10.

The present example, as is shown in FIG. 8-FIG. 10, is another example changing the shape of collars 2 in the embodiment 1.

A dental attachment 103 of this example also has, like the embodiments 1 and 2, an almost round outer shape of the yoke 11. Also, the outer shape surrounding collars 2 and the non-protruding portion 3 has a bigger diameter than the yoke 11 and the outer peripheral shape of the almost round shape of the concentric circle has a shape which is cut by four plural tangents contacting outer peripheral surface 115 of the yoke 11. Also, the parts which are not cut and left are four collars 2, and the parts which are cut are four non-protruding portion 3. The maximum outer diameter D1 including collars 2 and the outer diameter D2 of the non-protruding portion 3 in this example has the same size as D1 and D2 of the embodiment 1. The others are the same as the embodiment 1.

Because the dental attachment 103 of this example has the non-protruding portion 3 in four parts, the fluidity of the adhesive can be improved further than in the case of the embodiments 1 and 2. But, because the space of collars 2 becomes smaller than that of the embodiments 1 and 2, the undercut effect seems a little less than that of the embodiments 1 and 2. Still, because the outer shape of collars 2 has the arc shape of almost concentric circle of the yoke 11, processing can be relatively easily done.

Embodiment 4

In this example, an experiment to evaluate the connecting strength between the adhesive and the dental attachments 1, 102, 103 (test sample E1, E2, E3) of the embodiments 1, 2, and 3 is performed. Also, for comparison, two prior dental attachments (test sample C1, C2), are prepared and the same experiment is performed.

Each test sample E1, E2, and E3 has, as is mentioned above, the outer diameter D0 of yoke 11: 4.4 mm, the maximum outer diameter D2 of the collar: 4.9 mm and the maximum protruding portion: 0.25 mm.

Figure 11:
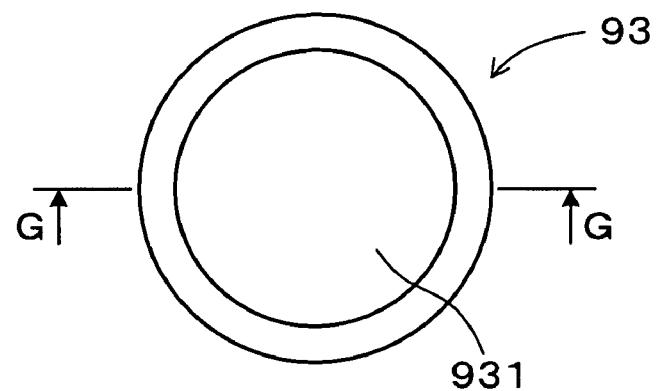
FIG. 11 is a plane view of a prior dental attachment as a comparative example of embodiment 4.
Figure 12:
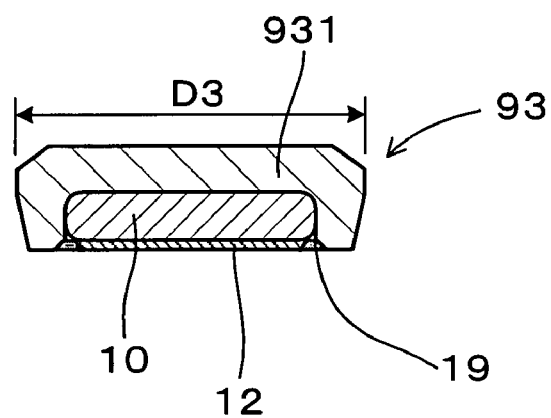
FIG. 12 is a cross section view of arrowed G-G of FIG. 10.

In one of the prior examples, a dental attachment 93 (test sample C2), as is shown in FIG. 11 and FIG. 12, a yoke 931 has no collars and the lateral part is a so called drum shape and the maximum outer diameter D3 is 4.4 mm. The magnetic element 10, the disk 12 and the welding portion 19 of the yoke 931 is the same as that of the dental attachment 1 of the embodiment 1.

Figure 13:
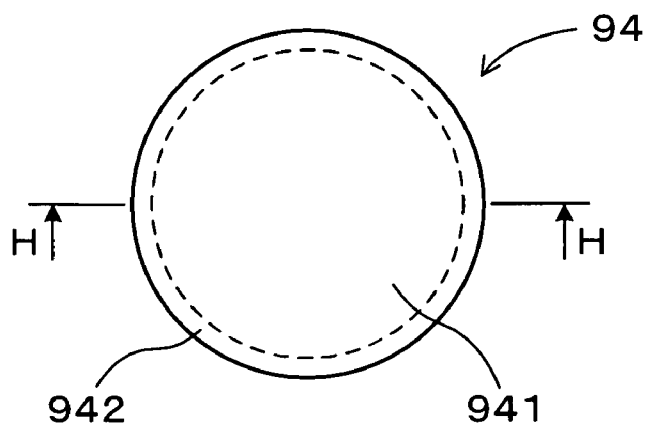
FIG. 13 is a plane view of another prior dental attachment as a comparative example of embodiment 4.
Figure 14:
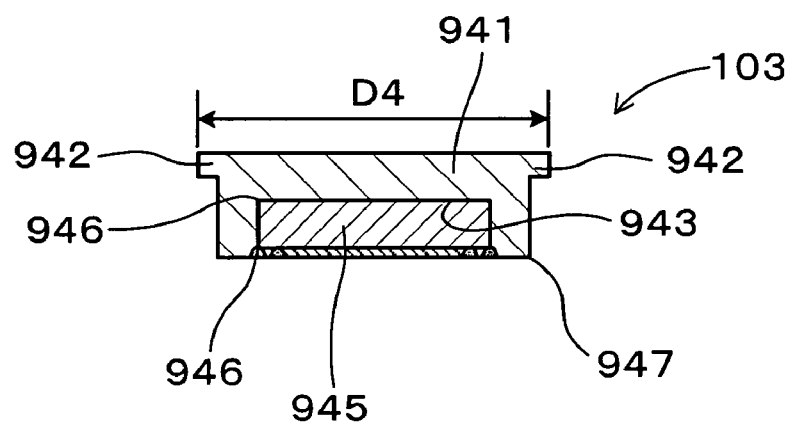
FIG. 14 is a cross section view of arrowed H-H of FIG. 13.

In another prior example, a dental attachment 94 (test sample C3), as is shown FIG. 13 and FIG. 14, the entire outer periphery of round shaped a yoke 941 has round shaped collars 942. The outer diameter D1 of collars 942 is 4.9 mm and the maximum projection amounts are 0.25 mm like test samples E1, E2 and E3. Also, in the dental attachment 94, as is shown in FIG. 14, both corners 946 of a housed magnetic element 945 are not R shape but right angled and a corner 947 of the surface having a recess 943 of the yoke 941 is also right angled and has no chamfer, which is different from the dental attachments 1, 102 and 103 of the embodiments 1 to 3.

Figure 15:
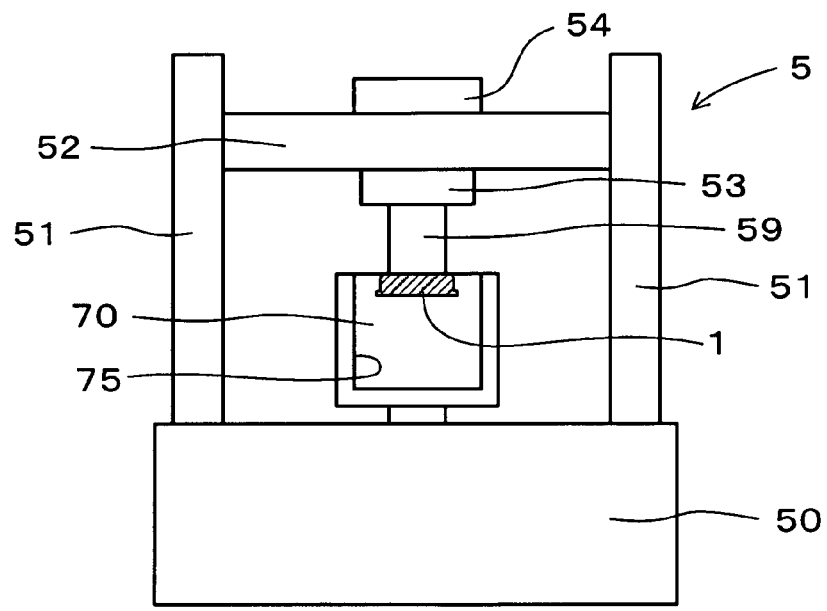
FIG. 15 is a diagram showing the structure of a trial machine of embodiment 4.

Next, an instron type tester 5, shown in FIG. 15, measures the connecting strength between the adhesive and the each test sample.

The tester 5 has a prop 51 on a holder 50 and an ascent and descent part 52 which can go up and down between them. Also, the ascent and descent part 52 has a clamp portion 53 which clamps a round bar 59 welded on the surface of the yoke of each test sample and a load cell 54 to measure load. Also, the holder 50 is made of the same material as the dental base (polymetacrylate (PMMA)) and has a column shape with diameter 20 mm and depth 20 mm and fixes a container 70 which has the hole 75 with diameter 15 mm at the center part.

First of all, after the hole 75 of the container 70 is filled with autopolymerizing resin (polymetacrylate (PMMA)) as the adhesive 7 and calcified, a hole with a diameter of 5 mm is made, and again the adhesive 7 is filled and each test sample welded with the round bar 59, the dental attachment 1 etc. is pushed into the adhesive 7, left for a set time and calcified.

Next, the container 70 with the joined test sample is put in a thermal cycle testing apparatus (NO FIG.) and a thermal test with 300 cycles of the temperature 4° C. and 60° C. each for one minute is performed. After that, the container 70 is set in the tester 5 and the round bar 59 welded with the test sample is fixed on the clamp portion 53.

Also, a tensile test with a pulling speed of 0.5 mm/min is performed and the tensile strength is valued as connecting strength.

The experimental results are shown in Table 1.

TABLE 1

| | Test sample | | | | |
|---|---|---|---|---|---|
| | The present invention | | | Prior example | |
| | E1 | E2 | E3 | C1 | C2 |
| Measured value (N) | 290 | 310 | 370 | 160 | 190 |

As Table 1 shows, the connecting strength of each test sample E1, E2, and E3 of the present invention has been much improved over that of prior samples C1 and C2.

Embodiment 5

Figure 16:
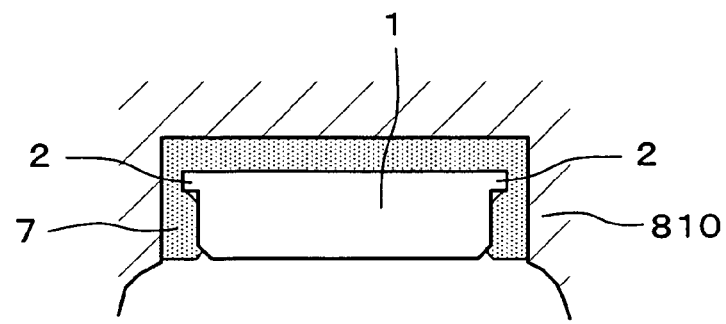
FIG. 16 is a diagram showing the condition that the dental attachment of present invention is fitted to the dental base in embodiment 5.
Figure 17:
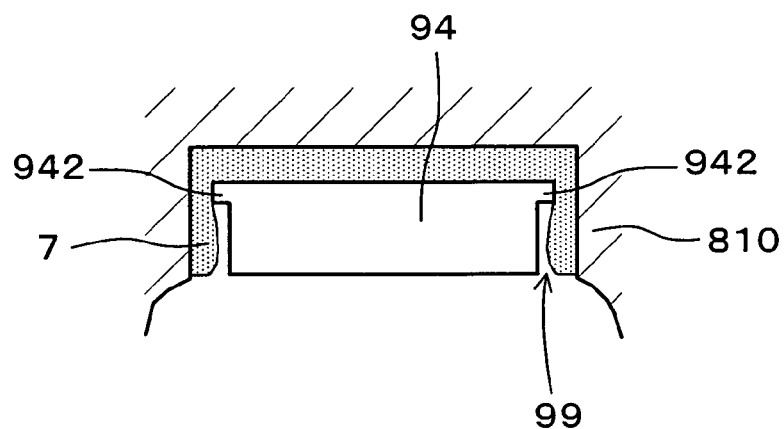
FIG. 17 is a diagram showing the condition that the prior dental attachment is fitted to the dental base in embodiment 5.

Next, FIG. 16 and FIG. 17 show the connecting condition with the adhesive 7 when the dental attachment 1 of the test sample E1 and the dental attachment 94 of the test sample C2 are practically connected with the dental base 810.

FIG. 16 shows the case of the dental attachment 1 of the test sample E1, which has collars 2. The adhesive 7 adequately goes around to both faces. This is, as is mentioned above, because by making the non-protruding portion 3, the flow ability effect of the adhesive 7 is sufficiently exerted.

FIG. 17 shows the case of the attachment 94 of test sample C2. The adhesive 7 does not adequately go around to the back face of collars 942. Also, a gap 99 is generated between the dental attachment 94 and the adhesive 7. This shows that without the non-protruding portion, adequate fluidity of the adhesive cannot be secured.

Embodiment 6

The present example changes the shape of the absorbing face of the dental attachment of the embodiment 1.

Figure 18:
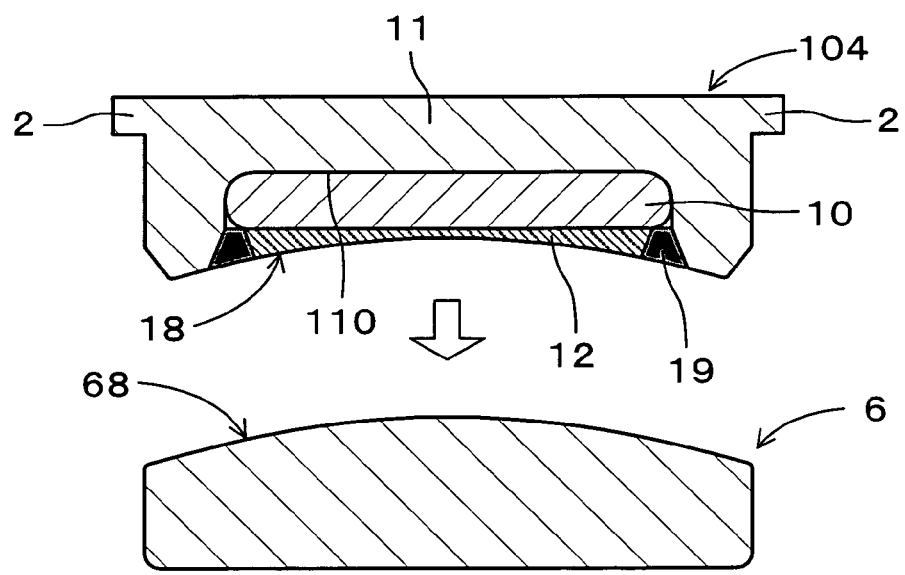
FIG. 18 is a cross section view of the dental attachment of embodiment 6 (This diagram corresponds to the diagram of arrowed A-A of FIG. 1)

That is, as is shown in FIG. 18, the dental attachment 104 of the present example uses a keeper which has a convex shaped absorbed face 68 as a facing keeper 6. Also, the absorbing face 18 facing the keeper 6 has a symmetric concave shape to the absorbed face 68 of the keeper 6 in the dental attachment 104.

In this case, because the absorbing face 18 of the dental attachment 104 has a concave shape which is symmetric to convex shaped absorbed face 68 of the keeper 6, both absorb well and both have a rotation function between them. Therefore, the denture can fluctuate and rotate along the keeper 6, without making a gap between the dental attachment 104 and the keeper 6. It also obtains the same operating effect as in embodiment 1.

The invention claimed is:

1. A dental attachment configured to be embedded in a denture base so as to face a keeper made of soft magnetic material in a tooth root, the dental attachment comprising:
    a magnetic element delivering magnetic attractive force;
    a yoke made of a soft magnet material and including a recess for housing the magnetic element; and
    a disk joined so as to close an opening of the recess with the magnet element housed in the recess;
    wherein the yoke includes a substantially circular disk-shaped portion and collars protruding radially outward from an outer peripheral surface of the disk-shaped portion of the yoke such that the yoke is formed as a single piece, and
    wherein the collars extend outwardly from a top surface of the disk-shaped portion of the yoke and are formed to be separated in at least two locations by separating parts having radially outward projection amounts from zero to 50% of a maximum projection amount of the collars.

2. The dental attachment according to claim 1, wherein the disk is made of the soft magnetic material.

3. The dental attachment according to claim 2, wherein the disk is joined with the yoke through a non-magnetic material part.

4. The dental attachment according to claim 1, wherein an outer peripheral shape of the collars and separating parts is substantially an oval, and a pair of the collars is formed in a major axis direction of the oval and a pair of the separating parts is formed in a minor axis direction of the oval.

5. The dental attachment according to claim 1, wherein an outer peripheral shape of the collars and separating parts is substantially a concentric circle, with a larger diameter than the circular disk-shaped portion of the yoke, cut by plural tangents contacting the outer peripheral surface of the circular disk-shaped portion of the yoke, a part not cut forming the collars, and a part cut forming the separating parts.

6. The dental attachment according to claim 5, wherein the plural tangents include two tangents formed opposite one another.

7. The dental attachment according to claim 5, wherein the plural tangents include four tangents substantially equally spaced.

8. The dental attachment according to claim 1, wherein the disk is welded to the yoke.

9. The dental attachment according to claim 1, further comprising:
    an absorbing face including a concave shape configured to fit symmetrically with a concave shape of a keeper in a tooth root,
    wherein the dental attachment can fluctuate and rotate along the keeper without making a gap between the dental attachment and the keeper.

10. The dental attachment according to claim 1, wherein the top surface of the yoke is opposite the disk.

11. The dental attachment according to claim 1, wherein the collars protrude a variable amount radially outward from an outer peripheral surface of the disk-shaped portion.

12. A dental system, comprising:
    a denture base including a recess therein;
    a dental attachment embedded in the recess of the denture base, the dental attachment comprising:
        a magnetic element delivering magnetic attractive force,
        a yoke made of a soft magnet material and including a recess for housing the magnetic element, and
        a disk joined so as to close an opening of the recess with the magnet element housed in the recess of the yoke,
        wherein the yoke includes a substantially circular disk-shaped portion and collars protruding radially outward from an outer peripheral surface of the disk-shaped portion of the yoke such that the yoke is formed as a single piece, and
        wherein the collars extend outwardly from a top surface of the disk-shaped portion of the yoke and are formed to be separated in at least two locations by separating parts having radially outward projection amounts from zero to 50% of a maximum projection amount of the collars; and
    adhesive positioned in the recess of the denture base to attach the dental attachment to the denture base, the adhesive extending around the separating parts of the yoke to be positioned on the outer peripheral surface of the disk-shaped portion of the yoke below an undercut created by the collars.

* * * * *